United States Patent [19]

Yacowitz

[11] Patent Number: 4,771,660

[45] Date of Patent: Sep. 20, 1988

[54] NEEDLE HOLDER

[76] Inventor: Harold Yacowitz, 211 Second Ave., Piscataway, N.J. 08854

[21] Appl. No.: 88,804

[22] Filed: Aug. 24, 1987

[51] Int. Cl.⁴ .......................... A61B 17/20; B26F 1/24
[52] U.S. Cl. ...................................... 81/9.22; 30/362; 604/47
[58] Field of Search ................... 81/9.22; 30/362, 366; 604/46, 47

[56] References Cited

U.S. PATENT DOCUMENTS

| 768,413 | 8/1904 | Wagner | 81/9.22 |
| 1,724,812 | 8/1929 | Waters | 81/9.22 |
| 4,159,659 | 7/1979 | Nightingale | 81/9.22 |

Primary Examiner—Roscoe V. Parker
Attorney, Agent, or Firm—Robert A. Green

[57] ABSTRACT

A tattoo needle and holder assembly comprising a tubular holder having a continuous needle-supporting trough extending therethrough to its lower end, the trough being open to the user and readily adapted to receive a tattoo needle. The lower end of the trough has a diameter sufficient to receive a tattoo needle with relatively snug fit and the needle can be readily guided into the lower end of the holder where it is positioned for use.

9 Claims, 3 Drawing Sheets

NEEDLE HOLDER

BACKGROUND OF THE INVENTION

Tattooing is performed by means of a sharp, small diameter needle or cluster of needles. The needle(s) are dipped in or otherwise supplied with tattoo pigment and then vibrated into or repeatedly inserted into the skin to be tattooed. The needle is carried in a tubular holder which includes means for vibrating the needle or repeatedly extending and retracting the needle. At the present time, the needle holders are of such construction that it is difficult to insert the needle and damage to the pointed end of the needle can occur. Such damage prevents proper operation of the tattooing procedure, and causes pain and or bleeding due to the dull points. The damage to the skin tissues by the dull needles causes inflammation and irritation, resulting in increased migratation of phagocytic white blood cells and other cells to the site of the tattoo. The phagocytic and other cells engulf the particles of tattoo pigment and carry the pigment away in the lymph and blood systems. The results of this inflammatory reaction is fading of the tattoo. Fading of tattoos is very undesirable, particularly in the case of animal tattoos which are used for identification procedures. Also, in human medical tattooing, the tattoo is sometimes used to mask scarred tissue or delineate sites in which cancerous tissue has been removed. Fading of tattoos is undesireable in these instances.

The present invention provides a holder for a tattoo needle in which the needle can be inserted easily and with substantially no opportunity for damaging the pointed end of the needle.

DESCRIPTION OF THE INVENTION

Figure 1:
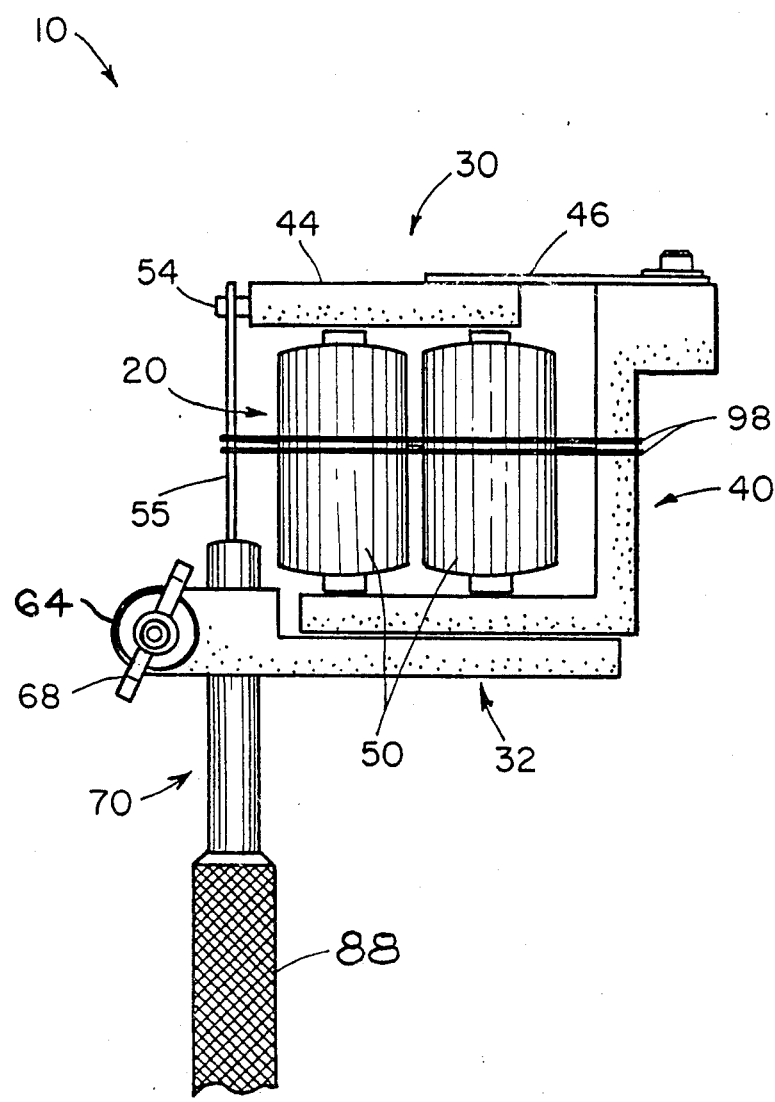
FIG. 1 is a side elevational view of apparatus embodying the invention.

The needle and needle holder of the invention may be used with commercially available tattooing apparatus 10 one form of which is shown in FIG. 1. The apparatus 10 includes, a U-shaped housing 20 placed on its side and made up of an upper leg 30, a lower leg 32 and a connecting side leg 40. The upper leg 30 is made up of a rigid armature bar 44 and a rearwardly projecting spring-like metal strip 46 which secures the bar 44 to the side leg 40. Electrical coils 50 are mounted on the housing 20 for use in causing the upper arm 30 to vibrate.

The leading end of the upper leg 30 and the front vertical surface of bar 44 carry a projecting pin 54 for coupling a tattooing needle 60 thereto as described below. The leading end of the lower leg 32 is formed with a horizontally disposed split ring 64 which is adapted to receive the needle holder of the invention and carries a threaded wing nut 68 for securing the needle holder 70 therein.

The apparatus 10 includes other parts which need not be described in detail.

Those skilled in the art will appreciate that other needle-driving apparatus can be devised or is available commercially.

Figures 2, 3:
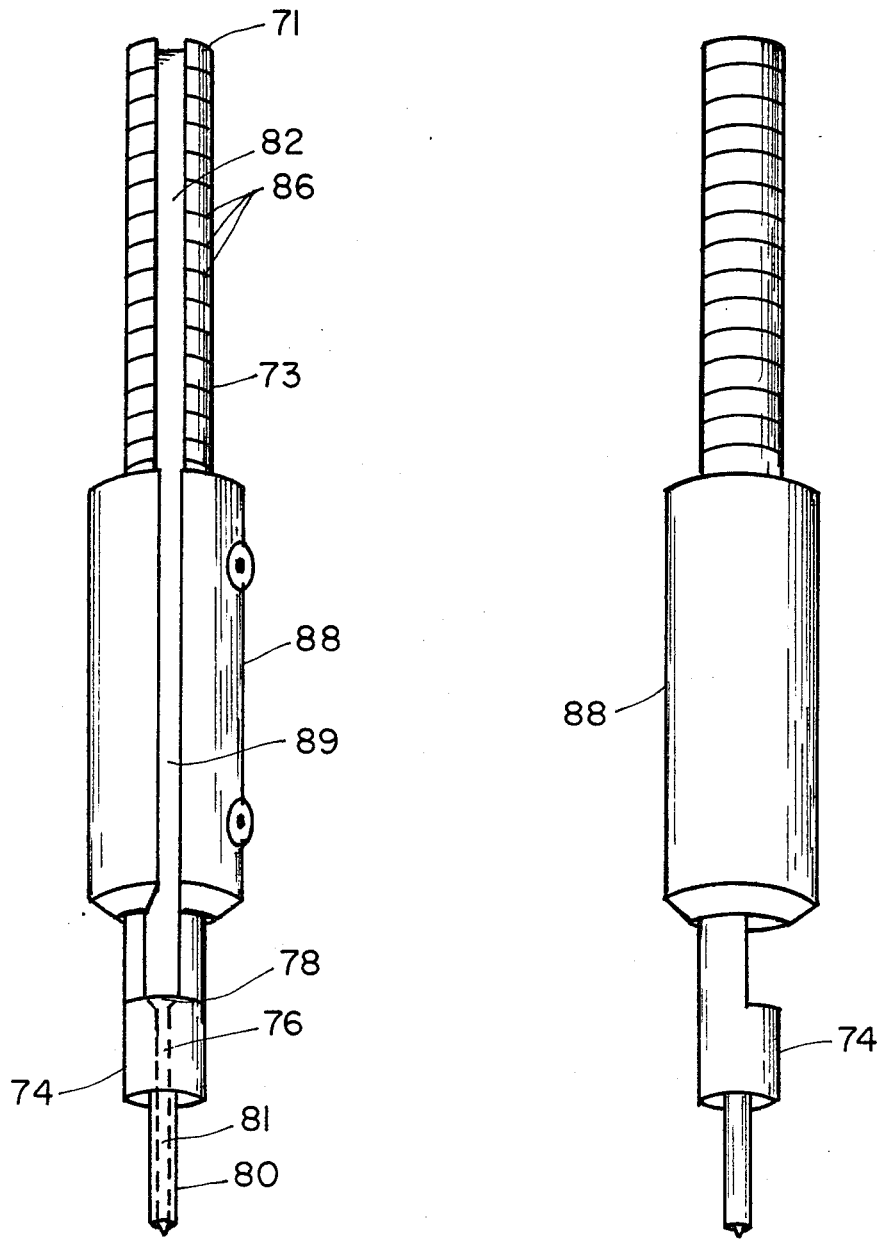
FIG. 2 is a front elevational view of a needle holder according to the invention.
FIG. 3 is a side view of the needle holder of FIG. 2.

Referring to FIGS. 2 and 3, the needle holder 70 comprises a hollow metal tube 73 of a suitable diameter having a slot 82 in its wall extending from the upper end 71 of the tube to near the lower end. A short length of the lower end of the tube 73 comprises a cylinder 74 which is not slotted but includes a through hole 76 which has a V-shaped upper opening 78.

A small-diameter hollow needle-guide tube 80, which receives the operating end of the tattooing needle, extends from the lower end of the cylinder 74 and has a through hole 81 which is aligned with and has the same diameter as through-hole 76 in cylinder 74.

Figure 4:
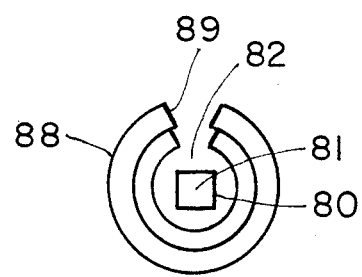
FIG. 4 is an end view of the needle holder of FIG. 2.

It can be seen that the trough or channel 82 in tube 73 and through-holes 76 and 81, with V-shaped opening 78, form an aligned continuous path for a needle. The lower end of the small end guide tube 80, as seen in FIG. 4, is generally square in cross-section for a purpose to be described.

Referring to FIGS. 2 and 3, the outer or rear surface of the upper portion of the hollow tube 73 is provided with spaced apart graduation marks 86 which represent a means of aligning the needle 60 with the holder 70 in a manner to be described. Each space between two graduations may represent one millimeter or the like.

For handling convenience, the tube 73 is provided with a surrounding metal sleeve 88 which extends along a portion of the tube but beginning well below the upper end of the tube and the graduations thereon. The sleeve carries a slot 89 which is aligned with the slot 82 in the wall of tube 73.

Figure 5:
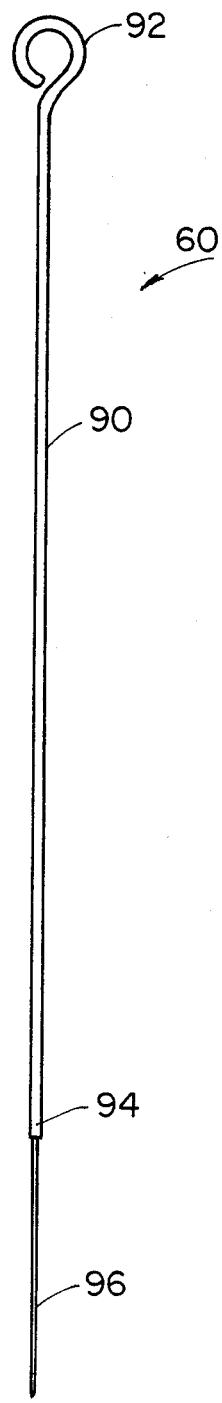
FIG. 5 is an elevational view of a needle used with the holder of FIG. 2.
Figure 6:
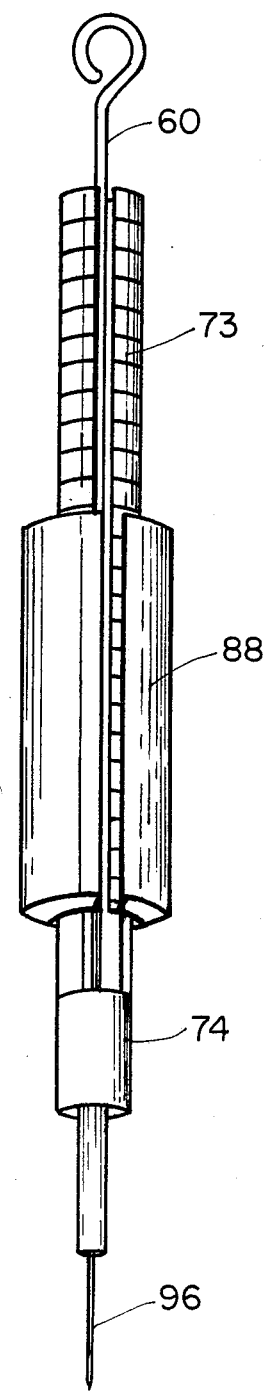
FIG. 6 is a perspective view of the needle holder of the invention with a needle in place therein.

Referring to FIG. 5, the needle 60 used with the holder 70 is of conventional construction and comprises a relatively rigid rod having a ring 92 at its upper end and the rest of the needle is of uniform small diameter to the lower operating end 94 to which is secured one or a plurality of individual filamentary needle-like members 96 which perform the tattooing function.

In using the holder 10, the needle 60 is placed within hollow tube 73 by being dropped or placed into the slot 82 in the wall of the tube 73 and in the sleeve. Since the holder is semicircular in structure and is open for most of its length it is easy to lay the needle in the trough formed thereby without damaging the needle. Next, the needle is guided by hand along the hollow tube 73 and then into the hollow tube through its V-shaped opening 78. Since the trough 82 and holes 76 and 81 are aligned and continuous and the hole in the opening 78 can be seen by the user the insertion of the operating end of the needle into tube 80 is accomplished easily and without damaging the leading, working end 96 of the needle. Typically, the needle is inserted until its lower end is aligned with the lower end of the tube 80 and then an adjustment can be made as follows.

The holder 70 carrying the needle 60 is now inserted in the ring 64 and the ring 92 at the upper end of the needle is placed on the pin 54 and the wing nut 68 is operated to grip the tube 73 and lock the holder 70 in the ring 64. Now, the position of the needle in the tube can be adjusted as desired by loosening the wing nut and with the needle held in place by having its upper ring firmly held on the pin 54, the holder can be moved up or down with respect to the needle while using the graduations as a guide aligned with the upper margin of the ring 64. When the desired setting is achieved, the wing nut is locked and the assembly is ready for performing a tattooing operation.

It is noted that elastic bands 98 are placed around the needle body and the U-shaped frame to pull the needle toward the frame and thereby position and hold the operating end 96 of the needle against a corner of the rectangular through-hole 81 in tube 80. This optimizes the tattooing operation.

The needle-holder of the invention has the following advantages:

1. It allows more rapid insertion of the tattooing needle;
2. It minimizes the possibility of damage to the needle;
3. It can be cleaned easily;
4. It can be used to precisely set the depth of needle penetration into the skin and this provides more permanent tattoos.
5. Permits precise setting of the depth of skin penetration which helps prevent pain and bleeding by preventing the needle from penetrating too deeply.

It is noted that the needle holder of the invention can be made of many materials such as nickel-plated iron, brass, bronze, aluminum or a hard plastic such as Teflon. However, stainless steel is preferred since this metal is durable, easily cleaned and does not corrode readily.

What is claimed is:

1. A tattoo needle and holder assembly comprising a tubular holder having a continuous needle-supporting trough extending therethrough from its upper end to its lower end, said trough being adapted to receive a tattooing needle having a main body portion and an operating end portion, and a hollow tube extending from the lower end of said tubular holder and adapted to receive the operating end portion of a tattoo needle with a relative snug fit, the opening into said hollow tube being visible to an operator through said trough and being shaped to facilitate entry of the operating end of a tattoo needle therein.

2. The apparatus defined in claim 1 wherein said trough and said hollow tube form a continuous aligned path for receiving a tattooing needle.

3. The apparatus defined in claim 1 wherein said hollow tube includes an upper end which communicates with said trough and includes a V-shaped opening which facilitates the insertion of a tattooing needle into said hollow tube.

4. The apparatus defined in claim 1 wherein said tubular holder includes an upper end which carries on its outer surface graduation markings for use in adjusting the position of a needle therein.

5. The needle and holder assembly defined in claim 1 and including a sleeve secured to a portion of said tubular holder.

6. The apparatus defined in claim 1 wherein the opening into said hollow tube has a generally square cross section whereby the tattoo needle may be securely positioned in one corner of the square during a tattooing operation.

7. The apparatus defined in claim 6 and including means for urging said tattoo needle into a corner of said opening and into said hollow tube.

8. The apparatus defined in claim 7 wherein said means comprises an elastic band which engages said tattoo needle and a portion of the apparatus.

9. Tattooing apparatus comprising a rigid frame, an arm of said frame being mounted to perform vibratory movement up and down, a tattoo needle assembly coupled to said frame and including an elongated rigid member having a continuous needle-supporting trough extending along its length from its upper end to its lower end, a tattoo needle seated in said elongated rigid member and having its upper end coupled to said arm whereby it can perform vibratory up and down movement, said elongated member including a hollow tube at its lower end in which the lower operating end of said needle is seated, said hollow tube having a generally square cross section, and means urging said operating end of said needle into one corner of said square hollow tube, said means comprising an elastic band wrapped around said needle and said frame, said rigid member including a lower end portion having a small-diameter through-hole of about the diameter of a tattoo needle, and a V-shaped opening into said lower end portion which can be seen by the user of the apparatus whereby insertion of the tattoo needle is facilitated.

* * * * *